(12) United States Patent
Mackool

(10) Patent No.: US 11,944,534 B1
(45) Date of Patent: Apr. 2, 2024

(54) INTRAOCULAR LENS WITH CHANNEL TO FACILITATE REMOVAL

(71) Applicant: Richard James Mackool, Sarasota, FL (US)

(72) Inventor: Richard James Mackool, Sarasota, FL (US)

( * ) Notice: Subject to any disclaimer, the term of this patent is extended or adjusted under 35 U.S.C. 154(b) by 0 days.

(21) Appl. No.: 18/213,927

(22) Filed: Jun. 26, 2023

(51) Int. Cl.
*A61F 2/16* (2006.01)

(52) U.S. Cl.
CPC .......... *A61F 2/1601* (2015.04); *A61F 2/1648* (2013.01); *A61F 2002/1681* (2013.01); *A61F 2002/1683* (2013.01); *A61F 2002/169* (2015.04); *A61F 2250/0097* (2013.01)

(58) Field of Classification Search
CPC .............. A61F 2/1601; A61F 2002/169; A61F 2002/1683; A61F 2250/0097
See application file for complete search history.

(56) References Cited

U.S. PATENT DOCUMENTS

| | | | |
|---|---|---|---|
| 5,800,533 A | 9/1998 | Eggleston et al. | |
| 7,455,691 B2 * | 11/2008 | Feingold | A61F 2/1602 623/6.49 |
| 8,087,777 B2 | 1/2012 | Rosenthal | |
| 9,095,424 B2 | 8/2015 | Kahook et al. | |
| 2004/0068317 A1 * | 4/2004 | Knight | A61F 2/1602 623/6.48 |
| 2005/0149184 A1 * | 7/2005 | Bogaert | A61F 2/1602 623/6.14 |
| 2007/0244560 A1 * | 10/2007 | Ossipov | A61F 2/2476 623/6.14 |
| 2014/0213958 A1 * | 7/2014 | Clauson | A61F 9/00781 604/8 |
| 2018/0153682 A1 | 6/2018 | Hajela et al. | |
| 2020/0166777 A1 * | 5/2020 | Rafaeli | G02C 7/049 |
| 2020/0400973 A1 * | 12/2020 | Larmagnac | G02C 7/041 |
| 2023/0240836 A1 * | 8/2023 | Irby | A61F 2/1627 623/6.22 |

* cited by examiner

*Primary Examiner* — Matthew J Lawson
*Assistant Examiner* — Aren Patel
(74) *Attorney, Agent, or Firm* — Collard & Roe, P.C.

(57) ABSTRACT

An intraocular lens has an upper surface and a lower surface, and comprising an optic portion, and at least one haptic portion connected to the optic portion and extending outward from the optic portion, and a channel disposed in the intraocular lens and having a first end being disposed in the optic portion and a second end disposed in the haptic portion. The channel extends generally radially outward from the optic portion into the haptic portion and is generally linear in a radial direction, but can have some curvature if desired. The channel is open to a top surface of the optic portion and haptic portion along the length of the channel or is disposed below the top surface of the optic portion and haptic portion, with openings in the top surface of the optic portion and haptic portion on each end of the channel.

13 Claims, 7 Drawing Sheets

INTRAOCULAR LENS WITH CHANNEL TO FACILITATE REMOVAL

BACKGROUND OF THE INVENTION

1. Field of the Invention

The present invention relates to an intraocular lens that is used to replace a patient's own lens, such as in cataract surgery. In particular, the invention relates to an intraocular lens having a channel that facilities removal from the capsule in the event that the lens needs to be replaced.

2. The Prior Art

Cataract surgery and other surgical procedures that treat lenticular tissue, such as, for example, the intraocular lens, are performed by making a small incision in the edge of the cornea, which provides access to the anterior chamber and to the anterior surface of the lens capsule, which is the membrane surrounding the lens. Afterward, a generally circular incision called a capsulorhexis is made through the anterior surface of the lens capsule to provide surgical access to the lens. An ophthalmic surgical instrument may be inserted through the incision and used to fragment the cataractous lens to facilitate its removal from the lens capsule. An artificial lens implant is then inserted into the capsule bag through the capsulotomy. The capsule walls cover the outer perimeter of the top surface of the artificial intraocular lens so that it does not protrude though the capsule.

If the patient's vision becomes impaired, or if there is a defect in the intraocular lens after placement, or a dislocation of the lens, it is often necessary to remove the artificial lens and replace it with a new one. This is normally done by inserting a cannula into the capsule around the lens, and injecting viscoelastic fluid into the capsule with a cannula. The viscoelastic fluid fills the capsule and loosens the adhesions of the lens to the capsule. The lens can then be lifted out of the capsular bag into the anterior chamber, which allows the lens to be bisected and removed or removed intact without damage to the capsule.

One of the drawbacks with this method is that it is very difficult to insert the cannula into the capsule underneath the capsule edge, due to the close fitting of the lens against the capsule walls. This procedure must be done very carefully, so as to not tear the capsule.

SUMMARY OF THE INVENTION

It is therefore an object of the invention to provide an intraocular lens that can be removed from the capsule if needed, in a simple and effective manner, and that reduces the risk of damage to the capsule.

This object is achieved by an intraocular lens having an upper surface and a lower surface, and comprising an optic portion, and at least one haptic connected to the optic portion and extending outward from the optic portion, and a channel disposed in the intraocular lens and having a first end being disposed in the optic portion and a second end disposed in the haptic portion. The channel extends generally radially outward from the optic portion into the haptic portion and is generally linear in a radial direction, but can have some curvature if desired.

The channel is small enough so that it does not interfere with the patient's vison. In one embodiment, the optic portion has a diameter of about 6 mm, and the channel extends between 1.0 mm and 1.5 mm across the optic portion and between 1.0 and 2.0 mm into the haptic portion. The capsule edge overlaps the edge of the optic portion, generally by 0.25-0.75 mm, but the channel is configured to extend beyond the edge of the optic portion so that it can be accessed through the capsule opening.

In one embodiment, the channel is open to a top surface of the optic portion and haptic portion along the length of the channel. This way, the physician merely has to slide the cannulate needle along the channel until it passes underneath the capsule edge, at which point the viscoelastic material can be injected into the capsule to loosen the lens.

In another embodiment, the channel is disposed below the top surface of the optic portion and haptic portion, with openings in the top surface of the optic portion and haptic portion on each end of the channel. The physician inserts the cannula needle into the opening in the optic portion, and the viscoelastic material can be injected into the channel, where it flows out of the opening in the haptic portion, which is under the capsule wall.

Preferably, the optic portion and haptic portion are formed in one piece, but a multi-part lens could also be constructed with the channel in either variant described above.

The channel preferably has a diameter of 0.2 to 0.5 mm, which is sufficient for the needle. However, a larger or smaller channel could be made. If a larger channel is desired, the optic portion can be constructed thicker in the region of the channel to accommodate the larger diameter without losing structural stability.

In toric lenses, there are often markers placed on the lens in order to show the surgeon the proper orientation of the lens during placement in the eye. In the present invention, markers can be placed along the sides of the channel to show the surgeon the orientation of the lens, as well as to indicate that the lens is a toric lens. In non-toric lenses, no markers are used, which also informs the surgeon that the lens is non-toric. Preferably, these markers are in the form of dots, and can be placed in any number, but 3-5 dots along the extent of the channel are normally used.

The intraocular lens of the present invention allows the physician to quickly and easily inject viscoelastic material into the lens capsule without damaging the capsule. In use, for the lens with the open channel, the physician takes a needle connected to cannula which is in turn connected to a source of viscoelastic, and slides the needle along the channel from the first end toward the second end until a distal end of the needle passes the capsule edge and is disposed within the capsule. The viscoelastic material is then injected through the cannula so that the viscoelastic exits the cannula within the capsule and inflates the capsule. At this point, the lens can be loosened from its adhesions to the capsule and can be moved through the capsule opening until it is disposed outside of the capsule. Once the lens is in the anterior chamber, it can be bisected for removal or removed intact. In the embodiment of the lens with the closed channel, the physician inserts the needle into the first opening and injects the viscoelastic material into the channel, where it flows along the channel to the second opening and exits the channel beneath the overlying lens capsule.

BRIEF DESCRIPTION OF THE DRAWINGS

Other objects and features of the present invention will become apparent from the following detailed description considered in connection with the accompanying drawings.

It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figures 1, 2:
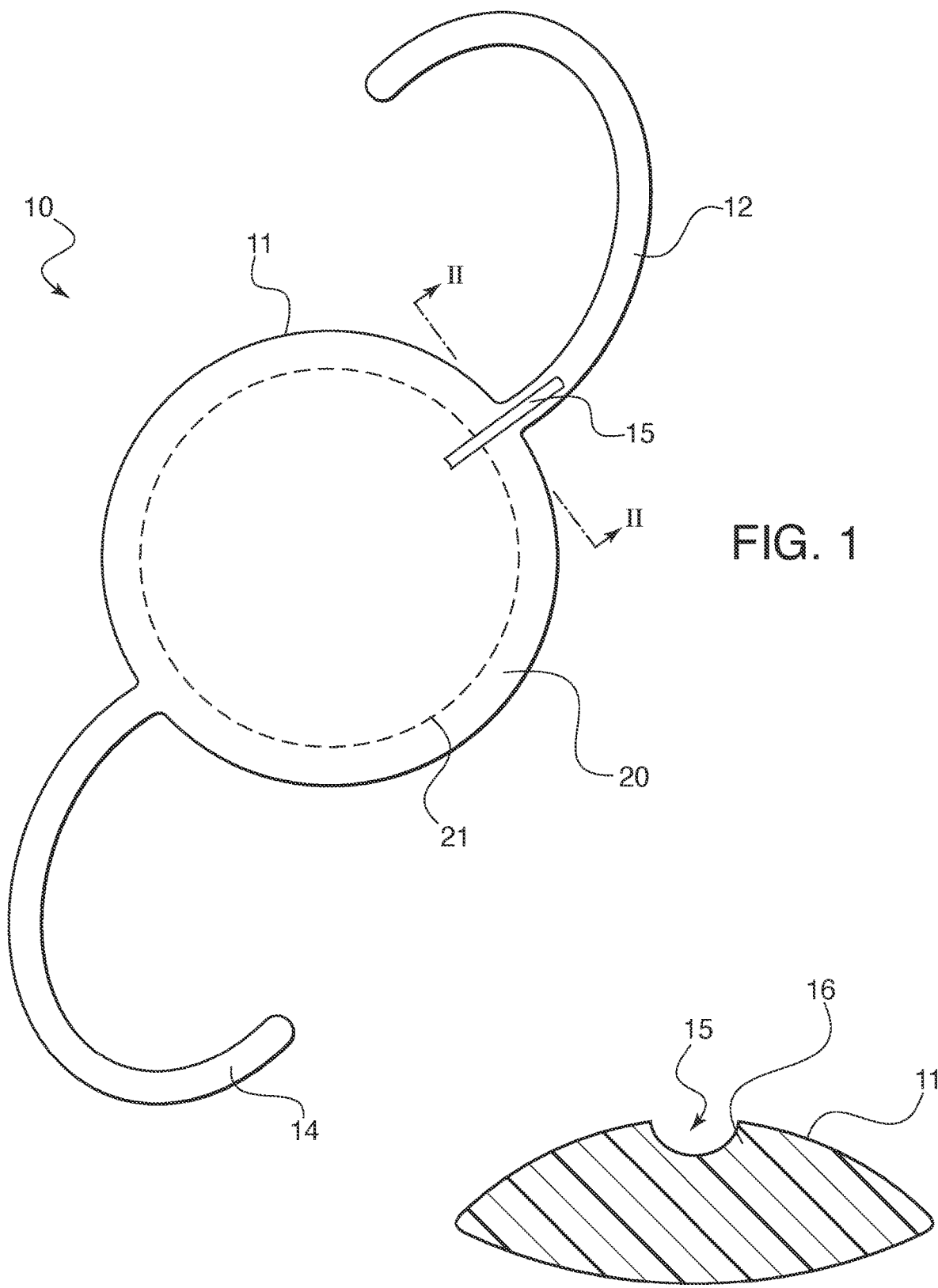
FIG. 1 shows a top view of a first embodiment of the lens according to the invention.
FIG. 2 shows a cross-section along lines II-II of FIG. 1.

Referring now in detail to the drawings and, in particular, FIGS. 1 and 2 show a first embodiment of the intraocular lens 10 according to the invention. Lens 10 is made of an optic portion 11 and two haptic portions 12, 14 in the form of curved arms. Haptic portions 12, 14 serve to position the optic portion 11 properly within the patient's lens capsule after the patient's natural lens has been removed. Optic portion 11 can be of any desired size but generally has a diameter of about 6 mm. During the procedure for extracting the cataract, a capsulorhexis is created in the lens capsule 20, leaving a circular opening with an edge 21. The overlap of the top surface of optic portion 11 by the lens capsule 20 bordered by the capsule edge 21 is shown in broken lines in FIG. 1, to illustrate the position of the intraocular lens 10 within the lens capsule.

Figure 6:
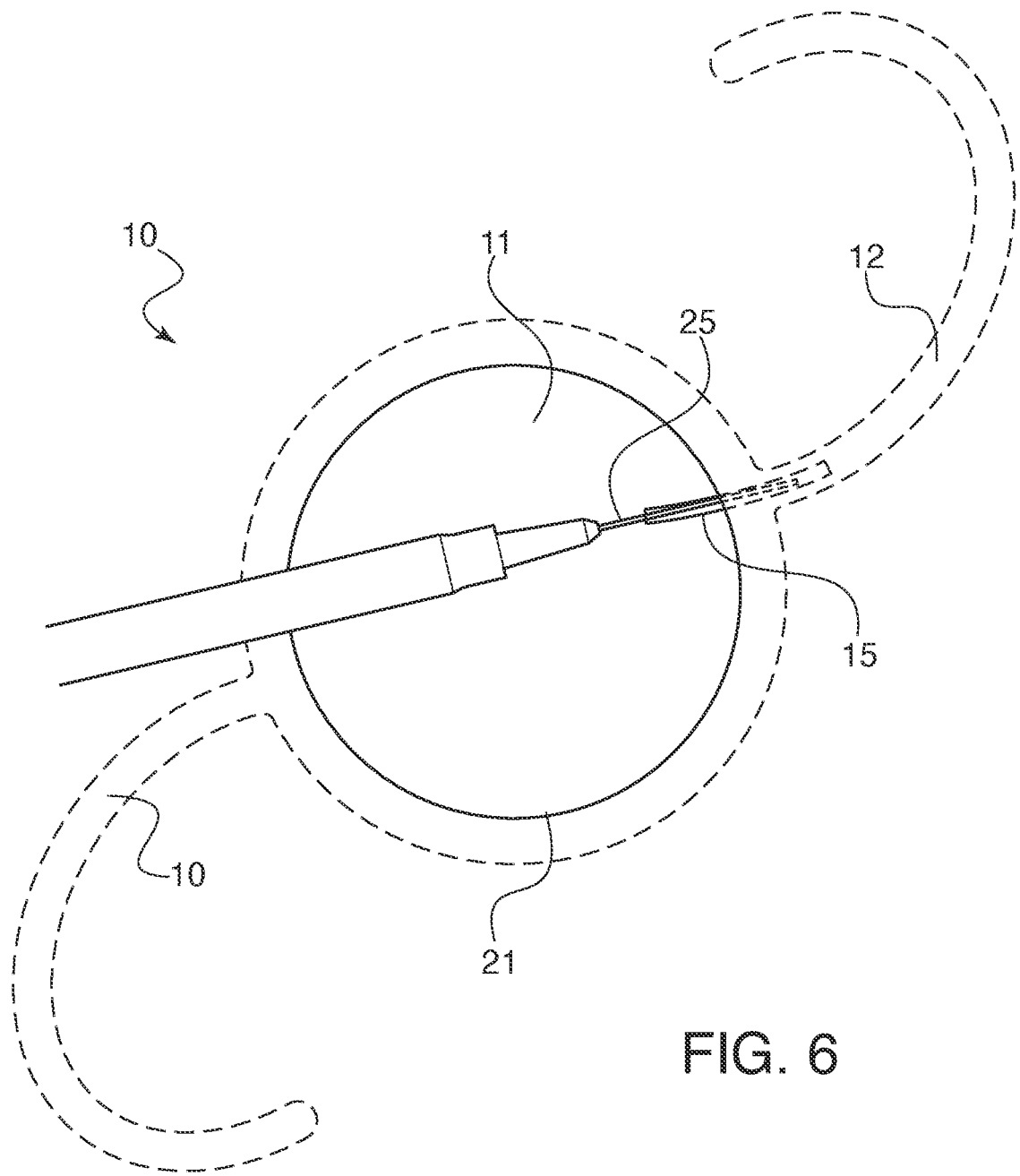
FIG. 6 shows the embodiment of FIG. 1 with a needle inserted.

In cases where lens 10 must be removed, it is very difficult to insert the cannula needle with the viscoelastic material underneath the capsule edge 24, because the edge rests firmly against optic portion 11 of lens 10. Thus, the lens 10 of the invention includes a channel 15, which spans the optic portion and haptic portion, and extends between a portion of the optic portion 11 that is exposed through the capsule opening, to an area underneath the capsule 20. The channel can be open to the top surface of the lens 10, as can be seen by the cross-sectional view of FIG. 2. This way, the cannula needle 25 with the viscoelastic material needs only to be placed on the proximal end of the channel that extends past the capsule edge 21, and then slid distally so that the needle passes under the capsule edge and adjacent capsule, such as shown in FIG. 6. The groove 15 enables the needle to pass much more easily underneath the capsule edge 21, as the needle is recessed into the lens 10. In FIG. 6, the lens is shown in broken lines, as it is not fully visible during surgery, as it is disposed within the capsule, except for the portion within the capsule opening. In this embodiment, lens 10 can be formed as a one-piece lens, with optic portion 11 and haptic portions 12 and 14 integrally molded. However, a multi-piece lens could also be made within the scope of the invention.

Figure 8:
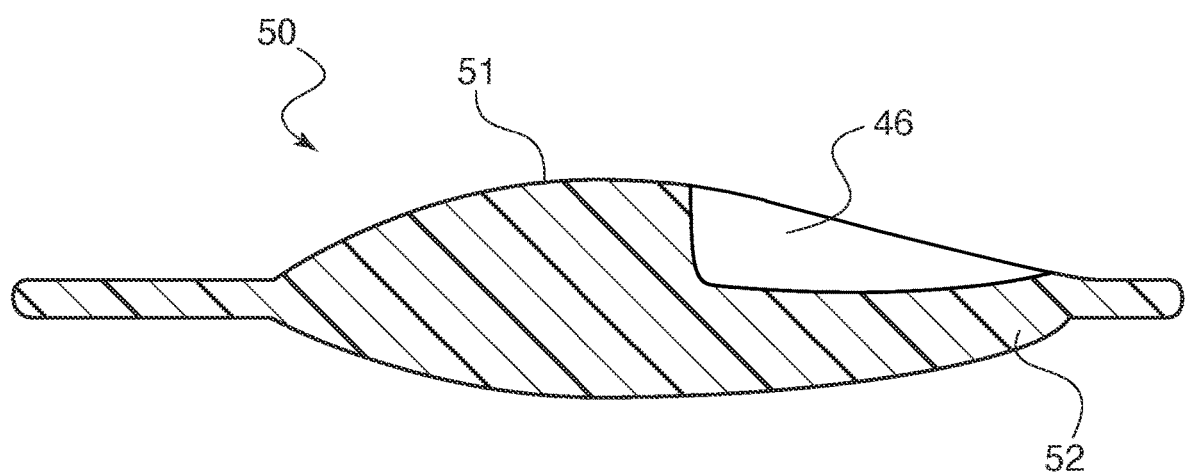
FIG. 8 shows a cross-sectional view of an alternative embodiment of the lens according to the invention.

The channel could be formed of any suitable dimensions, but is generally linear in a longitudinal direction, with a rounded bottom surface 16 the channel extends between 1.0 mm and 1.5 mm across the optic portion and between 1.0 and 2.0 mm across the haptic portion. Preferably the channel has a diameter of 0.2 to 0.5 mm, but could be made smaller or larger depending on the desired needle size. If a larger diameter channel is desired, an embodiment shown in FIG. 8 can be used. Here, the lens 50 is the same as the lens 10 except that the lens 50, including both optic portion 51 and haptic portion 52 could be thickened in this region so as to maintain stability of the lens, even with a deeper channel 55, such as shown by the cross-section in FIG. 8.

Figure 3:
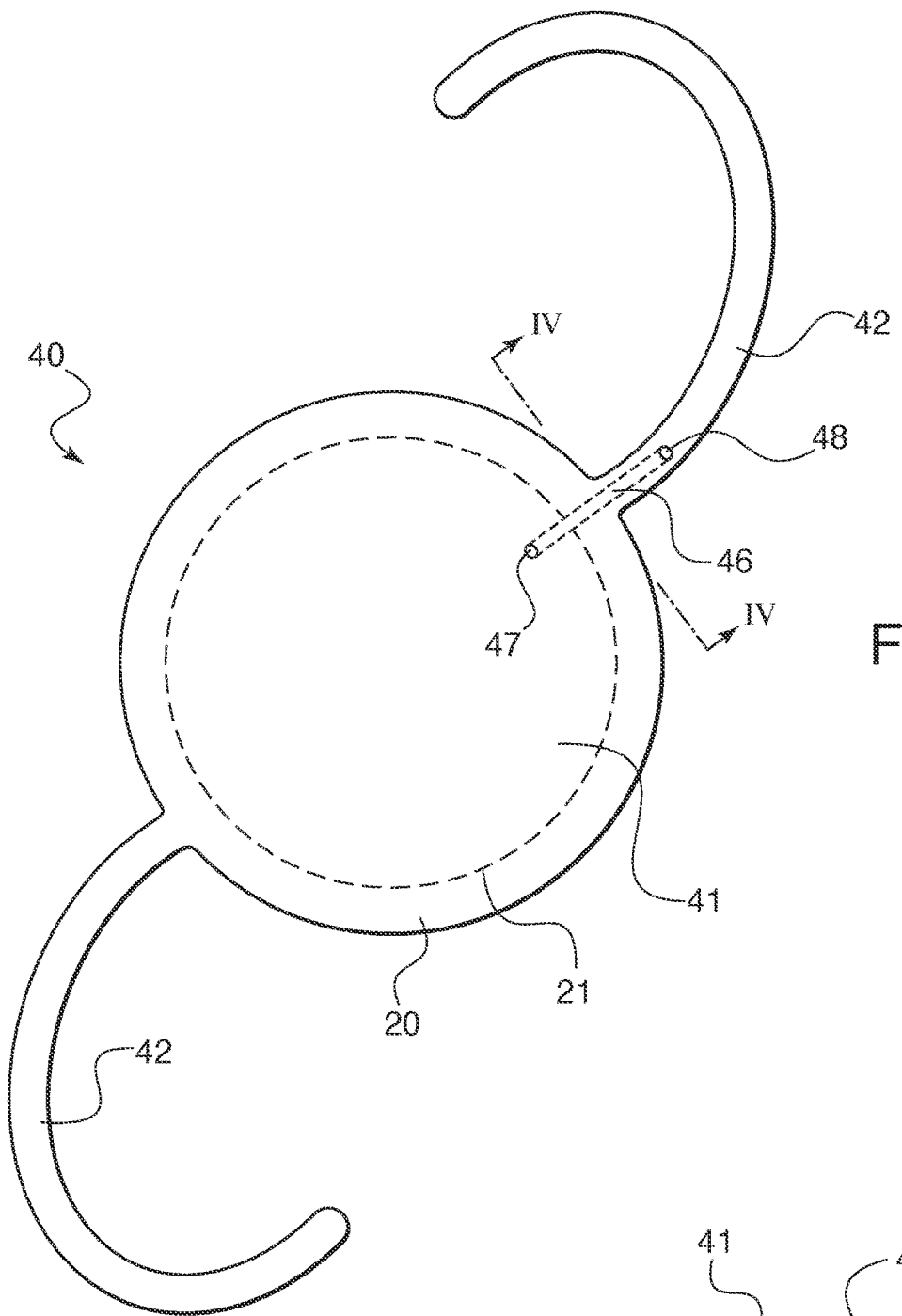
FIG. 3 shows a top view of a second embodiment of the lens according to the invention.
Figure 4:
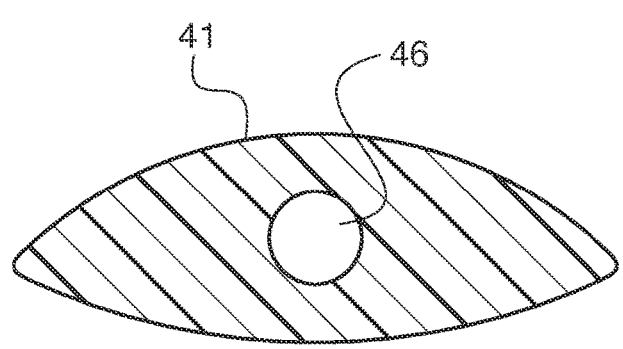
FIG. 4 shows a cross-section along lines IV-IV of FIG. 3.
Figure 5:
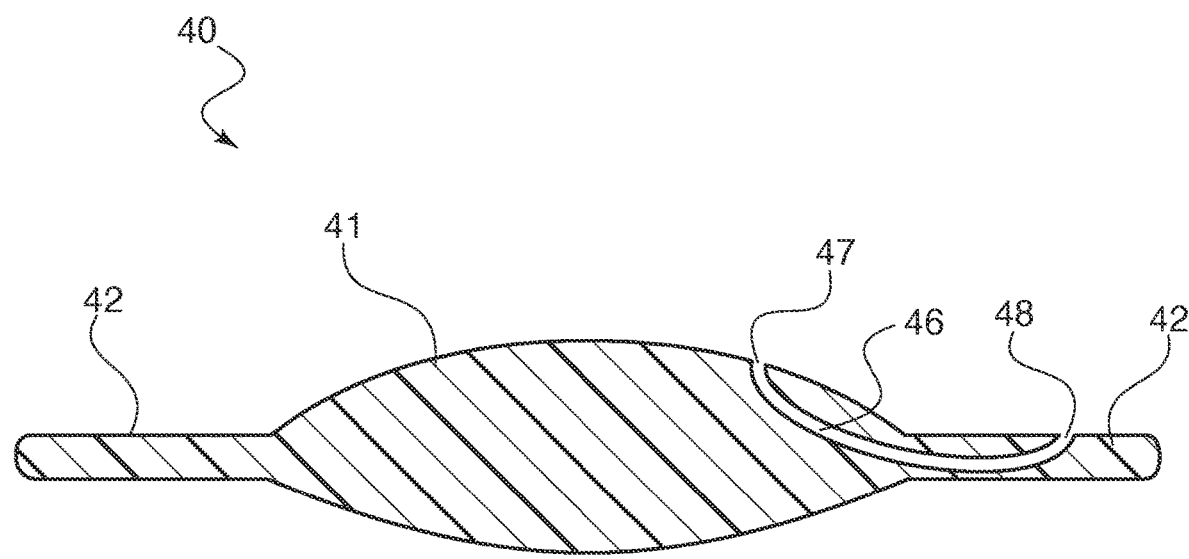
FIG. 5 shows a cross-section along lines V-V of FIG. 3.

An alternative embodiment of the invention is shown in FIGS. 3-5. Here, lens 40 also is formed of an optic portion 41 and two haptic portions 42 that extend radially out from optic portion 41 in the form of curved arms. Similar to lens 10, capsule 21 covers the outer edge of optic portion 41 up to a capsule edge 21 that overlaps the top surface of optic portion 41. Instead of an open groove, channel 46 is formed as a tunnel underneath the surface of lens 40, with a proximal opening 47 in the optic portion 41 that extends beyond the capsule wall and is exposed in the capsule opening, and a distal opening 48 in the haptic portion 42, within the capsule. As shown in FIG. 4, channel 46 has a round cross-section and is disposed in the center of the depth of lens but could be positioned closer to the top surface or bottom surface if desired. To accommodate both openings, channel 46 is curved in a linear cross-section, as shown in FIG. 5.

Figure 7:
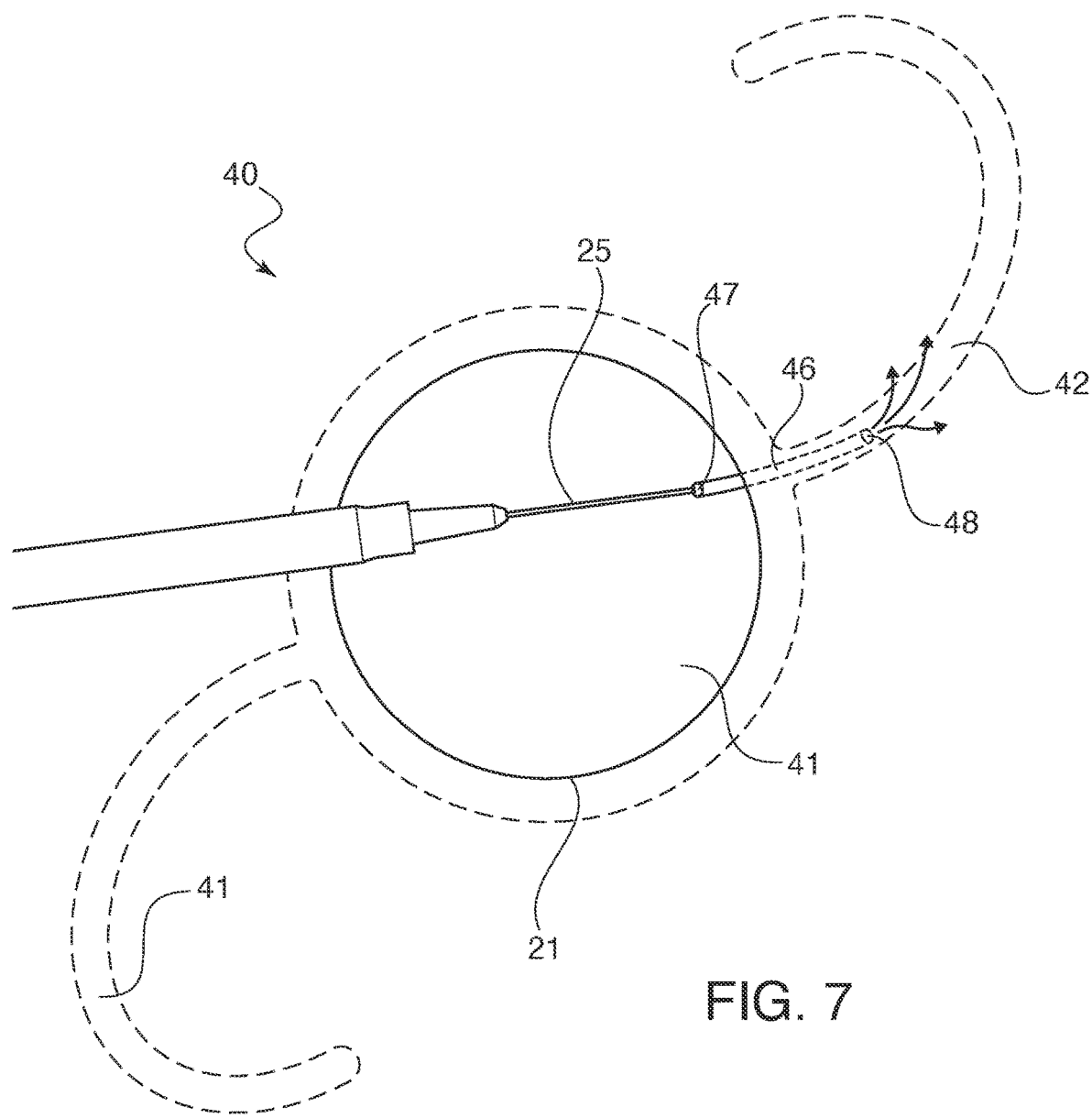
FIG. 7 shows the embodiment of FIG. 3 with a needle inserted.

FIG. 7 illustrates the procedure for injecting the viscoelastic material under the capsule wall with the lens 40. Here, the physician places the tip of the cannula needle into the proximal opening 47 and then injects the viscoelastic material into the channel 46. The material travels through the channel and exits distal opening 48, which is beneath the overlying lens capsule. This way, the physician does not have to try to slide the needle under the capsule edge 21. The proximal opening is exposed in the capsule opening and no further movement of the needle 25 is required in order to place the viscoelastic material beneath the capsule.

Figure 9:
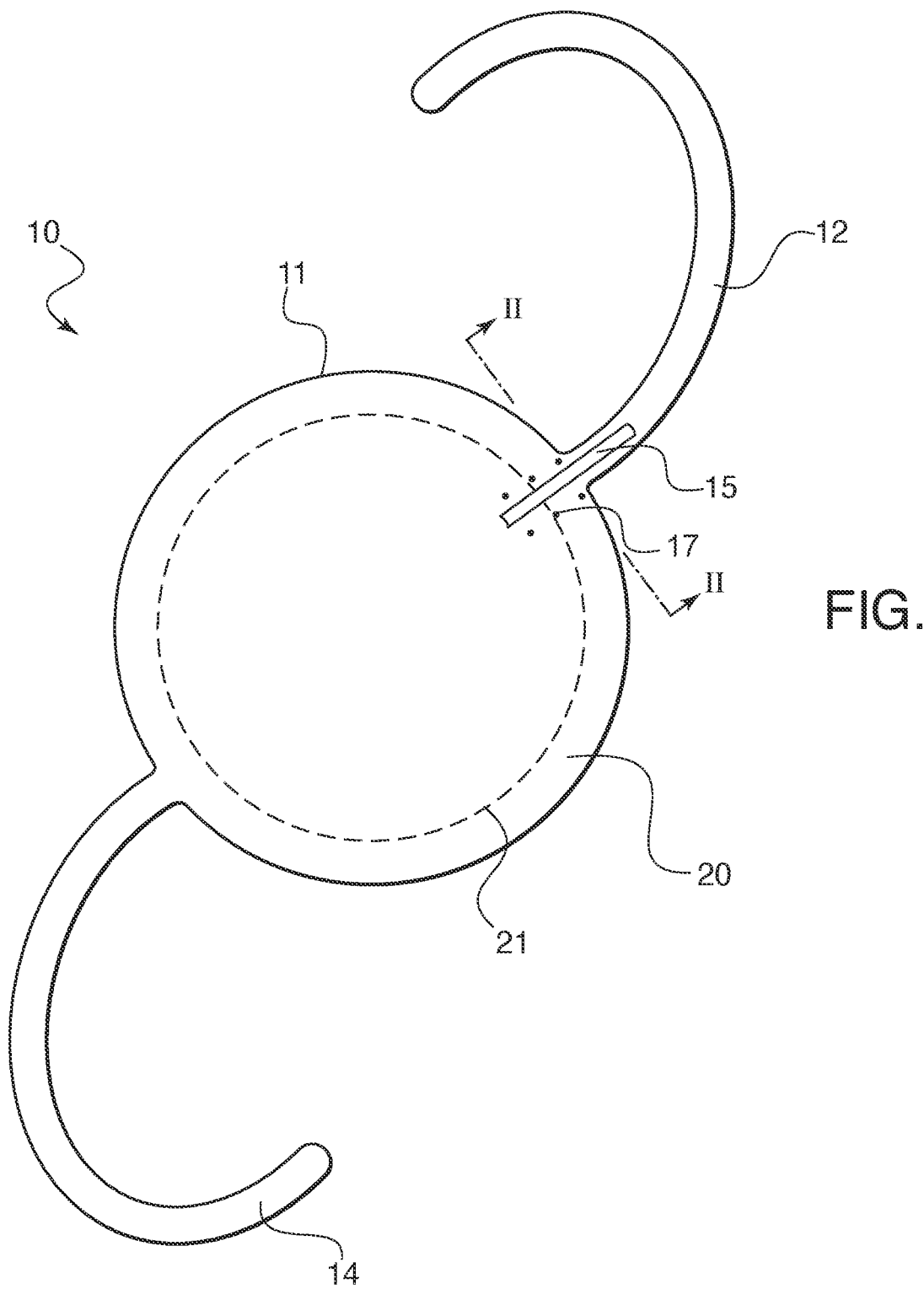
FIG. 9 shows another alternative embodiment of the lens according to the invention.

FIG. 9 shows the lens 10 according to the invention as a toric lens. Here, lens 10 is identical to the embodiment of FIG. 1, but indicators in the form of dots 17 are placed along both sides of channel 15, to indicate the orientation of lens 10 to the surgeon. Other types of markers could also be used. Dots 17 or other markers could also be used with lens 10, and located in any desired location or configuration. If the lens is non-toric, no indicators are required.

With all of the embodiments, once the viscoelastic material is in the capsule, it serves to loosen the adhesion of the peripheral optic and haptic portions from the capsule wall, so that the lens 10, 40 can be moved through the capsule opening and into the anterior chamber of the eye for bisection and removal in a standard procedure.

The intraocular lens of the present invention improves the physician's ability to inject the viscoelastic material into the capsule by eliminating the need to pry the capsule edge up from the optic with the needle prior to injection. The present invention also eliminates or reduces the risk of damage to the capsule because the needle is not applying any pressure to the capsule edge.

Accordingly, while only a few embodiments of the present invention have been shown and described, it is obvious that many changes and modifications may be made thereunto without departing from the spirit and scope of the invention.

What is claimed is:

1. An intraocular lens, comprising:
   an optic portion, and at least one haptic portion connected to the optic portion and extending outward from the optic portion, and a channel disposed in the intraocular lens and having a first end being disposed in the optic portion and a second end disposed in one of the at least one haptic portion, wherein the channel is in the form of an open groove that is open through a top surface of the optic portion and a top surface of the one haptic portion along an entire longitudinal extent of the channel.

2. The intraocular lens according to claim 1, wherein the channel extends radially through the optic portion into the haptic portion.

3. The intraocular lens according to claim 1, wherein the channel extends between 1.0 mm and 1.5 mm across the optic portion.

4. The intraocular lens according to claim 1, wherein the channel extends between 1.0 and 2.0 mm into the haptic portion.

5. The intraocular lens according to claim 1, wherein the optic portion and haptic portion are formed in one piece.

6. The intraocular lens according to claim 1, wherein the channel has a diameter of 0.2 to 0.5 mm.

7. The intraocular lens according to claim 1, wherein the optic portion has a diameter of about 6 mm.

8. The intraocular lens according to claim 1, further comprising at least one indicator marking disposed on the lens, to indicate the orientation of the lens.

9. The intraocular lens according to claim 8, wherein the at least one indicator marking comprises a series of dots extending adjacent the channel.

10. A method for injecting a substance beneath a lens capsule containing the intraocular lens of claim 1, the capsule having an anterior portion that has an opening with an edge that overlaps a periphery of the optic portion, comprising:

sliding a needle along the channel from the first end toward the second end until a distal end of the needle passes the capsule edge and is disposed within the capsule, and injecting a fluid through the needle so that the fluid exits the needle beneath the anterior portion of the capsule.

11. An intraocular lens, comprising:

an optic portion having a top surface, and at least one haptic portion connected to the optic portion and extending outward from the optic portion, the at least one haptic portion having a top surface that is adjacent the top surface of the optic portion, and a channel disposed in the intraocular lens and having a first end being disposed in the optic portion and a second end disposed in one of the at least one haptic portion, wherein the channel extends underneath the top surface of the optic portion and the top surface of the one haptic portion, and wherein the first end opens into the top surface of the optic portion, and the second end opens into the top surface of the one haptic portion.

12. A method for injecting a substance beneath a lens capsule containing the intraocular lens of claim 11, the capsule having an anterior opening with an edge that overlaps a periphery of the optic portion, comprising:

inserting a needle into the first opening, and injecting a fluid through the needle so that the fluid exits the needle within the channel, flows through the channel and exits the channel at the second end.

13. An intraocular lens, comprising:

an optic portion having an outer radial periphery, and at least one haptic portion connected to the optic portion and extending outward from the optic portion, and a channel disposed in the intraocular lens and extending radially from an interior part of the optic portion through the outer radial periphery of the optic portion, wherein the channel is in the form of an open groove that opens through a top surface of the optic portion along an entire longitudinal extent of the channel.

\* \* \* \* \*